US005691453A

United States Patent [19]
Wertz et al.

[11] Patent Number: 5,691,453
[45] Date of Patent: Nov. 25, 1997

[54] SEPARATION OF POLYMERIZED HEMOGLOBIN FROM UNPOLYMERIZED HEMOGLOBIN ON HYDROXYAPATITE USING HPLC

[75] Inventors: Curtis E. Wertz, Weymouth; Maria S. Gawryl, Charlestown, both of Mass.

[73] Assignee: Biopure Corporation, Cambridge, Mass.

[21] Appl. No.: 475,899

[22] Filed: Jun. 7, 1995

[51] Int. Cl.$^6$ .................. C07K 14/805; C07K 1/14; C07K 1/18; C07K 1/34
[52] U.S. Cl. .................. 530/385; 530/412; 530/414; 530/415; 530/418
[58] Field of Search ................... 530/385, 412, 530/414, 418, 415

[56] References Cited

U.S. PATENT DOCUMENTS

| | | | |
|---|---|---|---|
| Re. 32,089 | 3/1986 | Blatt et al. | 210/651 |
| 3,864,478 | 2/1975 | Bonhard | 424/101 |
| 3,944,391 | 3/1976 | Harris et al. | 23/230 B |
| 4,001,200 | 1/1977 | Bonsen et al. | 260/112.5 R |
| 4,059,512 | 11/1977 | Harris | 210/24 |
| 4,136,093 | 1/1979 | Bonhard et al. | 260/112.5 R |
| 4,336,248 | 6/1982 | Bonhard et al. | 424/101 |
| 4,341,867 | 7/1982 | Johansen | 435/187 |
| 4,376,059 | 3/1983 | Davis et al. | 252/316 |
| 4,439,357 | 3/1984 | Bonhard et al. | 260/112 |
| 4,468,330 | 8/1984 | Kamiyama et al. | 210/656 |
| 4,584,130 | 4/1986 | Bucci et al. | 260/112 |
| 4,780,210 | 10/1988 | Hsia | 210/638 |
| 4,857,636 | 8/1989 | Hsia | 530/385 |
| 4,861,867 | 8/1989 | Estep | 514/6 |
| 4,920,194 | 4/1990 | Feller et al. | 530/385 |
| 4,925,574 | 5/1990 | Hsia | 530/385 |
| 5,115,100 | 5/1992 | Wu et al. | 530/385 |
| 5,189,146 | 2/1993 | Hsia | 530/385 |
| 5,194,590 | 3/1993 | Sehgal et al. | 530/385 |
| 5,250,665 | 10/1993 | Kluger et al. | 530/385 |
| 5,296,465 | 3/1994 | Rausch et al. | 514/6 |
| 5,334,706 | 8/1994 | Przybelski | 530/385 |
| 5,364,932 | 11/1994 | Hsia | 530/385 |

FOREIGN PATENT DOCUMENTS 0 342 932   11/1989   European Pat. Off. .

OTHER PUBLICATIONS

Joo et al., "Studeies on the Peroxdase activity of Rabbit Hmoglobin," Korean Biochem. J., vol. 24, No. 6, pp. 564–571. (Abstract Only), 1991.

Tye et al., "Modification of Hemoglobin—Tetrameric Stabilization," Progress in Clinical and Biolgical Research, vol. 122, pp. 41–49. (Abstract Only), 1983.

Roe S., (1989) Protein Purification—Principles and Practice. Chapter 4: Seperation based on structure., Harris, E.L.V. and Angal, S. (eds), IRL Press, Oxford, pp. 175–243, especially pp. 238–242, 1989.

Huisman T.H.J., "Speration of Hemoglobins and Hmoglobin Chains By High–Perfromance Liquid Chromatography", J. of Chromatography, vol. 418, pp. 277–304, 1987.

Hiranuma et al., "Separation of Membrane Protein–Sodium Dodecyl Sulphate Complexes by High–Performance Liquid Chromatography on Hydroxyapatite," *Journal of Chromatography*, 515:399–406 (1990).

Inoue, Senya and Ohtaki, Nobuyuki, "Pyrophosphates as Biocompatible Packing Materials for High–Performance Liquid Chromatography," *Journal of Chromatography*, 645:57–65 (1993).

Gorbunoff, M. J., "The Interaction of Proteins with Hydroxyapatite: I. Role of Protein Charge and Structure," *Analytical Biochemistry*, 136:425–432 (1984).

Gorbunoff, M. J., "The Interaction of Proteins with Hydroxyapatite: II. Role of Acidic and Basic Groups," *Analytical Biochemistry*, 136:433–439 (1984).

Gorbunoff, M. J. and Timasheff, S. N., "The Interaction of Proteins with Hydroxyapatite: III. Mechanism," *Analytical Biochemistry*, 136:440–445 (1984).

Kawasaki, T., "Hydroxyapatite as a Liquid Chromatographic Packing," *Journal of Chromatography*, 544:147–184 (1991).

Benesch et al., "Hemoglobin Covalently Bridged Across the Polyphosphate Binding Site," *Biochem. and Biophys. Res. Comm.*, 63(4):1123–1129 (1975).

Feola et al., "Toxicity of Polymerized Hemoglobin Solutions," *Surg., Gynecol. & Obstet.*, 166:211–222 (1988).

Feola et al., "Complement Activation and the Toxicity of Stroma–Free Hemoglobin Solutions in Primates," *Circulatory Shock*, 25:275–290 (1988).

Huisman, "Separation of Hemoglobins and Hemoglobin Chains by High–Performance Liquid Chromatography," *J. Chromatogr.*, 418:277–304 (1987).

Huisman et al., "Studies on the Heterogeneity of Hemoglobin, The Use of Tris(Hydroxymethyl) Aminomethane–HCl Buffers in the Anion–Exchange Chromatography of Hemoglobins," *J. Chromatogr.*, 19:160–169 (1965).

Kramlova et al., "Fast Protein Liquid Chromatography of Pyridoxalated and Glutaraldehyde–Treated Human Haemoglobin," *J. Chromatogr.*, 249:403–404 (1982).

Simoni et al., "Evaluation of Anion–Exchange Liquid Chromatography for Purification of Hemoglobin from Peptides and Other Proteins," *Analytica Chimica Acta*, 249:169–183 (1991).

Sofer, "Chromatographic Removal of Pyrogens," *Bio/Technology*, pp. 1035–1037 (Dec. 1984).

White et al., "Toxicity of Human Hemoglobin Solution Infused into Rabbits," *J. Lab. Clin. Med.*, 108(2):121–131 (Aug. 1986).

*Primary Examiner*—Cecilia J. Tsang
*Assistant Examiner*—Anish Gupta
*Attorney, Agent, or Firm*—Hamilton, Brook, Smith & Reynolds, P.C.

[57] ABSTRACT

A method for producing a stable polymerized hemoglobin blood-substitute from blood. The method of this invention includes contacting a polymerized hemoglobin solution with a hydroxyapatite HPLC column and recovering the substantially pure polymerized hemoglobin.

18 Claims, No Drawings

SEPARATION OF POLYMERIZED HEMOGLOBIN FROM UNPOLYMERIZED HEMOGLOBIN ON HYDROXYAPATITE USING HPLC

BACKGROUND OF THE INVENTION

There exists a need for a blood-substitute to treat or prevent hypoxia resulting from blood loss (e.g., from acute hemorrhage or during surgical operations), resulting from anemia (e.g., pernicious anemia or sickle cell anemia), or resulting from shock (e.g., volume deficiency shock, anaphylactic shock, septic shock or allergic shock).

The use of blood and blood fractions as in these capacities as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and interdonor incompatibility.

Human hemoglobin, as a blood-substitute, possesses osmotic activity and the ability to transport and transfer oxygen, but it has the disadvantage of rapid elimination from circulation by the renal route and through vascular walls, resulting in a very short, and therefore, a typically unsatisfactory half-life. Further, human hemoglobin is also frequently contaminated with toxic levels of endotoxins, bacteria and/or viruses.

Non-human hemoglobin suffers from the same deficiencies as human hemoglobin. In addition, hemoglobin from non-human sources is also typically contaminated with proteins, such as antibodies, which could cause an immune system response in the recipient.

Previously, at least four other types of blood-substitutes have been utilized, including perfluorochemicals, synthesized hemoglobin analogues, liposome-encapsulated hemoglobin, and chemically-modified hemoglobin. However, many of these blood-substitutes have typically had short intravascular retention times, being removed by the circulatory system as foreign substances or lodging in the liver, spleen, and other tissues. Also, many of these blood-substitutes have been biologically incompatible with living systems.

Thus, in spite of the recent advances in the preparation of hemoglobin-based blood-substitutes, the need has continued to exist for a blood-substitute which has levels of contaminants, such as endotoxins, bacteria, viruses, phospholipids and non-hemoglobin proteins, which are sufficiently low to generally prevent an immune system response and any toxicological effects resulting from an infusion of the blood-substitute. In addition, the blood-substitute must also be capable of transporting and transferring adequate amounts of oxygen to tissue under ambient conditions and must have a good intravascular retention time.

Further, it is preferred that the blood-substitute 1) has an oncotic activity generally equivalent to that of whole blood, 2) can be transfused to most recipients without cross-matching or sensitivity testing, and 3) can be stored with minimum amounts of refrigeration for long periods.

SUMMARY OF THE INVENTION

The present invention relates to a method for producing a stable polymerized hemoglobin blood-substitute from whole blood. In particular, the invention relates to the separation of polymerized hemoglobin from a heterogeneous mixture of polymerized and unpolymerized hemoglobin employing a hydroxyapatite chromatographic column, such as an HPLC.

In one embodiment, the method involves separating a hemoglobin eluate from whole blood through one or more purification or reaction steps, optionally deoxygenating and subsequently contacting the eluate with a sulfhydryl compound to form an oxidation-stabilized deoxygenated hemoglobin solution, which is subsequently mixed with a cross-linking agent to form a polymerization reaction mixture. The polymerization reaction mixture is then separated in a chromatographic column packed with a hydroxyapatite, purifying the dimeric or tetrameric hemoglobin fractions from the higher molecular weight hemoglobin polymers. The polymerized hemoglobin solution thus formed is subsequently made physiologically acceptable, for use as a blood-substitute.

The advantages of this invention are numerous. One advantage is that the polymerized hemoglobin produced by the method of this invention has a high degree of purity in a single purification step with a shorter processing time than either dialfiltration or size exclusion. Furthermore, a greater yield of polymerized hemoglobin blood-substitute from the polymerized hemoglobin solution is achieved employing the claimed method than either diafiltration or ion exchange. An additional advantage is that the hemoglobin produced by the methods of this invention has a greater degree of purity than previous methods. Thus, the hemoglobin derived from one species can be successfully employed in a different species as a blood-substitute without the recipient species suffering significant side-effects.

DETAILED DESCRIPTION OF THE INVENTION

The features and other details of the process of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the present invention.

As set forth above, the invention relates to the separation of polymerized hemoglobin (Poly(Hb)) from a heterogeneous mixture of polymerized and unpolymerized hemoglobin employing a hydroxyapatite chromatographic column, such as an HPLC. Suitable hydroxyapatite materials include calcium phosphate hydroxides available in crystalline form from, for example, Sigma Chemical Co., as a suspension or gel. In a preferred embodiment the hydroxyapatite is obtained as a spherical macroporous ceramic particle from BioRad Laboratories or American International Chemical, Inc..

The chromatographic column containing hydroxyapatite is first prepared with a low ionic strength buffer (such as, between about 10 mM to about 60 mM) which facilitates binding of the Poly(Hb). In particular, preferred low ionic strength buffers contain low concentrations of phosphate or chloride. The concentrated Poly(Hb) solution is injected into the column and binds. Successive elution with buffers of increasing concentration of the buffer are used to elute first the non-polymerized hemoglobin (e.g., the dimeric 32 kDa protein) and the tetramer (the 64 kDa protein) and, subsequently, the desired polymerized hemoglobin. Examples of higher buffer concentrations include between about 100 mM to about 1M.

Examples of suitable buffers include phosphate buffers (such as potassium phosphate, sodium phosphate and ammonium phosphate) and chloride buffers (such as, sodium chloride and potassium chloride).

A suitable chromatography column can be Waters AP-1 column dry packed with hydroxyapatite to a bed height of 7.5 cm and diameter of 1 cm with a total volume of about 6 cc.

In a preferred embodiment, the hydroxyapatite column is first prepared by eluting with a low concentration potassium phosphate buffer (20 mM and pH 7.0). The poly(Hb) is injected onto the column in a concentrated form and binds. Separate elution of the non-polymer and stable 64 kD polymer is accomplished by mixing a portion of another higher concentration potassium phosphate buffer (200 mM and pH 7.0) into the first buffer and eluting the column. The phosphate concentration of this non-polymer and 64 kD polymer eluting mixed buffer is 61 mM and elution continues until the elution of Hb from the column stabilizes at a low level. The column is then eluted with the high potassium phosphate concentration buffer to elute the separate polymer (Hb) which is collected for further processing.

In this example, a heterogeneous mixture of hemoglobin polymers which contain 33.2% non-polymer (i.e., the 32 kD dimer and 64 kD tetramer) and 66.8% polymer of a combination of polymers larger than 64 kDa can be purified to a mixture containing less than about 2.6% non-polymer in a single 30 minute chromatography step. The combined non-polymer is eluted at a concentration of 91.1% with 8.9% polymerized hemoglobin.

As defined herein, a blood-substitute is a hemoglobin-based oxygen carrying composition for use in humans, mammals and other vertebrates, which is capable of transporting and transferring oxygen to vital organs and tissues, at least, and can maintain sufficient intravascular oncotic pressure. A vertebrate is as classically defined, including humans, or any other vertebrate animals which uses blood in a circulatory system to transfer oxygen to tissue. Additionally, the definition of circulatory system is as classically defined, consisting of the heart, arteries, veins and microcirculation including smaller vascular structures such as capillaries.

A blood-substitute formed by the method of invention has levels of endotoxins, phospholipids, foreign proteins and other contaminants which will not result in a significant immune system response and which are non-toxic to the recipient. Preferably, a blood-substitute is ultrapure. Ultrapure as defined herein, means containing less than about 0.5 EU/ml of endotoxin, less than about 3.3 nmoles/ml phospholipids and little to no detectable levels of non-hemoglobin proteins, such as serum albumin or antibodies.

The term "endotoxin" refers to the cell-bound lipopolysaccharides, produced as a part of the outer layer of gram-negative bacterial cell walls, which under many conditions are toxic. When injected into animals, endotoxins can cause fever, diarrhea, hemorrhagic shock, and other tissue damage. Endotoxin unit (EU) has been defined by the United States Pharmacopeial Convention of 1983, page 3014, as the activity contained in 0.1 nanograms of U.S. reference standard lot EC-5. One vial of EC-5 contains 10,000 EU. Examples of suitable means for determining endotoxin concentrations in a blood-substitute include the method "Kinetic/Turbidimetric Limuus Amebocytic Lystate (LAL) 5000 Methodology" developed by Associates of Cape Cod, Woods Hole, Mass.

Stable polymerized hemoglobin, as defined herein, is a hemoglobin-based oxygen carrying composition which does not substantially increase or decrease in molecular weight distribution and/or in methemoglobin content during storage periods at suitable storage temperatures for periods of two months or more, and preferably for periods of two years or more, when stored in a low oxygen environment. Suitable storage temperatures are, for example, between about 0° C. and about 40° C. The preferred storage temperature range is between about 0° C. and about 25° C.

A suitable low oxygen environment is defined as the cumulative amount of oxygen in contact with the blood-substitute, over a storage period of at least one year which will result in a methemoglobin concentration of less than about 15% by weight in the blood-substitute. The cumulative amount of oxygen includes oxygen which has leaked into the blood-substitute packaging and the original oxygen content of the blood-substitute and packaging.

The polymerized hemoglobin is preferably prepared by a method comprising mixing blood with an anticoagulant to form a blood solution and then washing the red blood cells in the blood solution to separate small plasma proteins from the red blood cells. The method also includes the steps of separating the washed red blood cells from the white blood cells and then disrupting the red blood cells to release hemoglobin and form a hemoglobin solution. Non-hemoglobin components in the hemoglobin solution are subsequently separated from the hemoglobin solution by molecular weight fractionation on 100 kD and 30 kD nominal molecular weight cut-off ultrafilters and high performance liquid chromatography (HPLC) to form a hemoglobin eluate. The hemoglobin eluate is then deoxygenated and subsequently contacted with a sulfhydryl compound to form an oxidation-stabilized deoxygenated hemoglobin solution, which is subsequently mixed with a cross-linking agent to form a polymerization reaction mixture. Such a process is disclosed in U.S. Ser. No. 08/484,775, filed Jun. 7, 1995, which is a Continuation-in-Part of copending U.S. patent application Ser. No. 08/458,916, filed on Jun. 2, 1995, entitled "METHOD FOR PRODUCING ULTRAPURE STABLE POLYMERIZED HEMOGLOBIN BLOOD-SUBSTITUTE," by Carl W. Rausch, et al., which is a Continuation of U.S. patent application Ser. No. 08/409,337, filed Mar. 23, 1995. That application is also a Continuation-in-Part of U.S. patent application Ser. No. 08/209,949, filed Mar. 11, 1994, which is a Continuation of U.S. patent application Ser. No. 07/820,153, filed Jan. 13, 1992, now U.S. Pat. No. 5,296,465, which is a Continuation of U.S. patent application Ser. No. 07/119,121, filed Nov. 10, 1987, now U.S. Pat. No. 5,084,558, which is a Continuation-in-Part of U.S. patent application Ser. No. 07/107,421, filed Oct. 13, 1987, now abandoned, which is a Continuation-in-Part of U.S. patent application Ser. No. 06/928,345, filed Nov. 10, 1986, now abandoned. The teachings of the patents and patent applications noted above are incorporated herein by reference in their entirety. The polymerization reaction mixture is then stabilized and subjected to the hydroxyapatite purification.

Throughout this method, from the red blood cell (RBC) collection until hemoglobin polymerization, blood solution, RBCs and hemoglobin are maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at 10±2° C.

Portions of the components for the process for preparing a stable polymerized hemoglobin blood-substitute are sufficiently sanitized to produce a sterile product. Sterile is as defined in the art, specifically, that the solution meets United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Inconel.

Suitable RBC sources include human blood, bovine blood, ovine blood, porcine blood, blood from other vertebrates and transgenically-produced hemoglobin, such as the transgenic Hb described in *BIO/TECHNOLOGY*, 12: 55–59 (1994).

The blood can be collected from live or freshly slaughtered donors. One method for collecting bovine whole blood is described in U.S. Pat. Nos. 5,084,558 and 5,296,465, issued to Rausch et al. It is preferred that the blood be collected in a sanitary manner.

At or soon after collection, the blood is mixed with at least one anticoagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution.

It is understood that the blood solution source can be from a freshly collected sample or from an old sample, such as expired human blood from a blood bank. Further, the blood solution could previously have been maintained in frozen and/or liquid state. It is preferred that the blood solution is not frozen prior to use in this method.

In another embodiment, prior to introducing the blood solution to anticoagulants, antibiotic levels in the blood solution, such as penicillin, are assayed. Antibiotic levels are determined to provide a degree of assurance that the blood sample is not burdened with an infecting organism by verifying that the donor of the blood sample was not being treated with an antibiotic. Examples of suitable assays for antibiotics include a penicillin assay kit (Difco, Detroit, Mich.) employing a method entitled "Rapid Detection of Penicillin in Milk". It is preferred that blood solutions contain a penicillin level of less than or equal to about 0.008 units/ml. Alternatively, a herd management program to monitor the lack of disease in or antibiotic treatment of the cattle may be used.

Preferably, the blood solution is strained prior to or during the anticoagulation step, for example by straining, to remove large aggregates and particles. A 600 mesh screen is an example of a suitable strainer.

The RBCs in the blood solution are then washed by suitable means, such as by diafiltration or by a combination of discrete dilution and concentration steps with at least one solution, such as an isotonic solution, to separate RBCs from extracellular plasma proteins, such as serum albumins or antibodies (e.g., immunoglobulins (IgG)). It is understood that the RBCs can be washed in a batch or continuous feed mode.

Acceptable isotonic solutions are as known in the art and include solutions, such as a citrate/saline solution, having a pH and osmolarity which does not rupture the cell membranes of RBCs and which displaces plasma portion of the whole blood. A preferred isotonic solution has a neutral pH and an osmolarity between about 285–315 mOsm. In a preferred embodiment, the isotonic solution is composed of an aqueous solution of sodium citrate dihydrate (6.0 g/l) and of sodium chloride (8.0 g/l).

Water which can be used in the method of invention include distilled water, deionized water, water-for-injection (WFI) and/or low pyrogen water (LPW). WFI, which is preferred, is deionized, distilled water that meets U.S. Pharmacological Specifications for water-for-injection. WFI is further described in *Pharmaceutical Engineering*, 11, 15–23 (1991). LPW, which is preferred, is deionized water containing less than 0.002 Eu/ml.

It is preferred that the isotonic solution be filtered prior to being added to the blood solution. Examples of suitable filters include a Millipore 10,000 Dalton ultrafiltration membrane, such as a Millipore Cat #CDUF 050 G1 filter or A/G Technology hollow fiber, 10,000 Dalton (Cat #UFP-10-C-85).

In a preferred embodiment, RBCs in the blood solution are washed by diafiltration. Suitable diafilters include microporous membranes with pore sizes which will separate RBCs from substantially smaller blood solution components, such as a 0.1 μm to 0.5 μm filter (e.g., a 0.2 μm hollow fiber filter, Microgon Krosflo II microfiltration cartridge). Concurrently, filtered isotonic solution is added continuously (or in batches) as makeup at a rate equal to the rate (or volume) of filtrate lost across the diafilter. During RBC washing, components of the blood solution which are significantly smaller in diameter than RBCs, or are fluids such as plasma, pass through the walls of the diafilter in the filtrate. RBCs, platelets and larger bodies of the diluted blood solution, such as white blood cells, are retained and mixed with isotonic solution, which is added continuously or batchwise to form a dialyzed blood solution.

In a more preferred embodiment, the volume of blood solution in the diafiltration tank is initially diluted by the addition of a volume of a filtered isotonic solution to the diafiltration tank. Preferably, the volume of isotonic solution added is about equal to the initial volume of the blood solution.

In an alternate embodiment, the RBCs are washed through a series of sequential (or reverse sequential) dilution and concentration steps, wherein the blood solution is diluted by adding at least one isotonic solution, and is concentrated by flowing across a filter, thereby forming a dialyzed blood solution.

RBC washing is complete when the level of plasma proteins contaminating the RBCs has been significantly reduced (typically, at least about 90%). Typically, RBC washing is complete when the volume of filtrate drained from diafilter 34 equals about 300%, or more, of the volume of blood solution contained in the diafiltration tank prior to diluting the blood solution with filtered isotonic solution. Additional RBC washing may further separate extracellular plasma proteins from the RBCs. For instance, diafiltration with 6 volumes of isotonic solution may remove at least about 99% of IgG from the blood solution.

The dialyzed blood solution is then exposed to means for separating the RBCs in the dialyzed blood solution from the white blood cells and platelets, such as by centrifugation.

It is understood that other methods generally known in the art for separating RBCs from other blood components can be employed. For example, sedimentation, wherein the separation method does not rupture the cell membranes of a significant amount of the RBCs, such as less than about 30% of the RBCs, prior to RBC separation from the other blood components.

Following separation of the RBCs, the RBCs are lysed by a means for lysing RBCs to release hemoglobin from the RBCs to form a hemoglobin-containing solution. Lysis means can use various lysis methods, such as mechanical lysis, chemical lysis, hypotonic lysis or other known lysis methods which release hemoglobin without significantly damaging the ability of the Hb to transport and release oxygen.

In yet another embodiment, recombinantly produced hemoglobin, such as the recombinantly produced hemoglobin described in *Nature*, 356: 258–260 (1992), can be processed in the method of invention in place of RBCs. The bacteria cells containing the hemoglobin are washed and separated from contaminants as described above. These bacteria cells are then mechanically ruptured by means known in the art, such as a ball mill, to release hemoglobin from the cells and to form a lysed cell phase. This lysed cell phase is then processed as is the lysed RBC phase.

Following lysis, the lysed RBC phase is then ultrafiltered to remove larger cell debris, such as proteins with a molecular weight above about 100,000 Daltons. Generally, cell debris include all whole and fragmented cellular components with the exception of Hb, smaller cell proteins, electrolytes, coenzymes and organic metabolic intermediates. Acceptable ultrafilters include, for example, 100,000 Dalton filters made by Millipore (Cat #CDUF 050 H1) and made by A/G Technology (Needham, Mass..; Model No. UFP100E55).

It is preferred that ultrafiltration continues until the concentration of Hb in the lysed RBC phase is less than 8 grams/liter (g/l) to maximize the yield of hemoglobin available for polymerization. Other methods for separating Hb from the lysed RBC phase can be employed, including sedimentation, centrifugation or microfiltration.

The Hb ultrafiltrate can then be ultrafiltered to remove smaller cell debris, such as electrolytes, coenzymes, metabolic intermediates and proteins less than about 30,000 Daltons in molecular weight, and water from the Hb ultrafiltrate. Suitable ultrafilters include a 30,000 Dalton ultrafilter (Millipore Cat #CDUF 050 T1 and/or Armicon, #540 430).

The concentrated Hb solution can then be directed into one or more parallel chromatographic columns to further separate the hemoglobin by high performance liquid chromatography from other contaminants such as antibodies, endotoxins, phospholipids, enzymes and viruses. Examples of suitable media include anion exchange media, cation exchange media, hydrophobic interaction media and affinity media. In a preferred embodiment, chromatographic columns contain an anion exchange medium suitable to separate Hb from non-hemoglobin proteins. Suitable anion exchange mediums include, for example, silica, alumina, titania gel, cross-linked dextran, agarose or a derivatized moiety, such as a polyacrylamide, a polyhydroxyethyl-methacrylate or a styrene divinylbenzene, that has been derivatized with a cationic chemical functionality, such as a diethylaminoethyl or quaternary aminoethyl group. A suitable anion exchange medium and corresponding eluants for the selective absorption and desorption of Hb as compared to other proteins and contaminants, which are likely to be in a lysed RBC phase, are readily determinable by one of reasonable skill in the art.

In a more preferred embodiment, a method is used to form an anion exchange media from silica gel, which is hydrothermally treated to increase the pore size, exposed to γ-glycidoxy propylsilane to form active epoxide groups and then exposed to $C_3H_7(CH_3)NCL$ to form a quaternary ammonium anion exchange medium. This method is described in the *Journal of Chromatography*, 120:321–333 (1976), which is incorporated herein by reference in its entirety.

Chromatographic columns are first pre-treated by flushing with a first eluant which facilitates Hb binding. Concentrated Hb solution is then injected onto the medium in the columns. After injecting the concentrated Hb solution, the chromatographic columns are then successively washed with different eluants to produce a separate, purified Hb eluate.

In a preferred embodiment, a pH gradient is used in chromatographic columns to separate protein contaminants, such as the enzyme carbonic anhydrase, phospholipids, antibodies and endotoxins from the Hb. Each of a series of buffers having different pH values, are sequentially directed to create a pH gradient within the medium in the chromatographic column. It is preferred that the buffers be filtered, such as with a 10,000 Dalton depyrogenation membrane. The buffers used to separate Hb should have a low ionic strength such that elution of Hb and non-hemoglobin contaminants is generally dependent upon pH and not significantly dependent upon ionic strength. Typically, buffers with an ionic concentration of about 50 mM, or less, have suitable low ionic strengths.

The first buffer transports the concentrated Hb solution into the medium in the chromatographic columns and facilitates binding of the Hb to the medium. The second buffer then adjusts the pH within the columns to eluate contaminating non-hemoglobin components while maintaining the Hb bound to the medium. The third buffer then eluates the Hb. The Hb eluate is then collected. It is preferred that the Hb eluate be directed through a sterile filter. Suitable sterile filters include 0.22 μm filters, such as a Sartorius Sartobran Cat #5232507 G1PH filter.

In a preferred embodiment, the first 3%-to-4% of the Hb eluate and the last 3%-to-4% of the Hb eluate are directed to waste to provide assurance of the purity of the Hb eluate.

Wherein the chromatographic columns are to be reused, contaminating non-hemoglobin proteins and endotoxin, remaining in the columns, are then eluted by a fourth buffer.

The use of pH gradients to separate Hb form non-hemoglobin contaminants is further described in copending U.S. patent application Ser. No. 08/473,497, filed Jun. 7, 1995, which is incorporated herein by reference in its entirety.

In a preferred embodiment, the first buffer is a tris-hydroxymethyl aminomethane (Tris) solution (concentration about 20 mM; pH about 8.4 to about 9.4). The second buffer is a mixture of the first buffer and a third buffer, with the second buffer having a pH of about 8.2 to about 8.6. The third buffer is a Tris solution (concentration about 50 mM; pH about 6.5 to about 7.5). The fourth buffer is a NaCl/Tris solution (concentrations about 1.0M NaCl and about 20 mM Tris; pH about 8.4 to about 9.4, preferably about 8.9–9.1). It is particularly preferred that the pH of the second buffer be between about 8.2 and about 8.4.

Typically, the buffers used are at a temperature between about 0° C. and about 50° C. Preferably, buffer temperature is about 12.4±1.0° C. during use. In addition, the buffers are typically stored at a temperature of about 9° C. to about 11° C.

The Hb eluate is then preferably deoxygenated prior to polymerization to form a deoxygenated Hb solution (hereinafter deoxy-Hb) by means that substantially deoxygenate the Hb without significantly reducing the ability of the Hb in the Hb eluate to transport and release oxygen, such as would occur from denaturation or formation of oxidized hemoglobin (met Hb).

In one embodiment, the Hb eluate is deoxygenated by gas transfer of an inert gas across a phase membrane. Such inert gases include, for example, nitrogen, argon and helium. It is understood that other means for deoxygenating a solution of hemoglobin, which are known in the art, can be used to deoxygenate the Hb eluate. Such other means, can include, for example, nitrogen sparging of the Hb eluate, chemical scavenging with reducing agents such as N-acetyl-L-cysteine (NAC), cysteine, sodium dithionite or ascorbate, or photolysis by light.

Following elution from the chromatographic column, the Hb eluate is preferably concentrated to improve the efficiency of the process. The Hb eluate is recirculated through an ultrafilter to concentrate the Hb eluate to form a concentrated Hb solution. Suitable ultrafilters include, for example, 30,000 or less Dalton ultrafilters (e.g., Millipore Helicon, Cat #CDUF050G1 or Amicon, Cat #540430). Typically, concentration of the Hb eluate is complete when the concentration of Hb is between about 100 to about 120 gl. While concentrating the Hb eluate, the Hb eluate temperature is preferably maintained at approximately 8°–12° C.

Buffer is then directed into the Hb solution, which is preferably concentrated, to adjust the ionic strength of the Hb solution to enhance Hb deoxygenation. It is preferred that the ionic strength be adjusted to between about 150 meq/l and about 200 meq/l to reduce the oxygen affinity of the Hb in the Hb solution. Suitable buffers include buffers with a pH that will not result in significant denaturing of the Hb protein but will have an ionic strength sufficiently high to promote Hb deoxygenation. Examples of suitable buffers include saline solutions with a pH range of about 6.5 to about 8.9. A preferred buffer is an aqueous 1.0M NaCl, 20 mM Tris solution with a pH of about 8.9.

Preferably, the resulting buffered Hb solution is then recirculated through the ultrafilter, to again concentrate the Hb solution to improve the efficiency of the process. In a preferred embodiment, concentration is complete when the concentration of Hb is about 100 g/l to about 120 g/l.

During deoxygenation the Hb solution is circulated through a suitable phase transfer membrane. Appropriate phase transfer membranes include, for example, a 0.05 μm polypropylene hollow fiber microfilter (e.g., Hoechst-Celanese Cat #5PCM-107). Concurrently, a counterflow of an inert gas is passed across the phase transfer membrane. Suitable inert gases include, for example, nitrogen, argon and helium. Gas exchange across phase transfer membrane thereby strips oxygen out of the Hb solution.

Deoxygenation continues until the $pO_2$ of the Hb solution is reduced to a level wherein the oxygenated Hb (oxyhemoglobin or $HbO_2$) content in the Hb solution is about 20% or less. In a preferred embodiment, the $HbO_2$ content in the Hb solution is about 10% or less.

During deoxygenation, the temperature of the Hb solution is typically maintained at a level that will balance the rate of deoxygenation against the rate of methemoglobin formation. Temperature is maintained to limit methemoglobin content to less than 20%. An optimum temperature will result in less than about 5% methemoglobin content, and preferably less than about 2.5% methemoglobin content, while still deoxygenating the Hb solution. Typically, during deoxygenation the temperature of the Hb solution is maintained between about 19° C. and about 31° C.

During deoxygenation, and subsequently throughout the remaining steps of the method of invention, the Hb is maintained in a low oxygen environment to minimize oxygen absorption by the Hb and to maintain an $HbO_2$ content of less than about 20%, preferably less than about 10%.

The deoxygenated-Hb is then preferably equilibrated with a low oxygen content storage buffer, containing a sulfhydryl compound, to form an oxidation-stabilized deoxy-Hb. Suitable sulfhydryl compounds include non-toxic reducing agents, such as N-acetyl-L-cysteine (NAC) D,L-cysteine, γ-glutamyl-cysteine, glutathione, 2,3-dimercapto-1-propanol, 1,4-butanedithiol, thioglycolate, and other biologically compatible sulfhydryl compounds. The oxygen content of a low oxygen content storage buffer must be low enough not to significantly reduce the concentration of sulfhydryl compound in the buffer and to limit oxyhemoglobin content in oxidation stabilized deoxy-Hb to about 20% or less, preferably less than about 10%. Typically, the storage buffer has a $pO_2$ of less than about 50 torr.

In a preferred embodiment, the storage buffer should have a pH suitable to balance Hb polymerization and methemoglobin formation, typically between about 7.6 and about 7.9.

The amount of a sulfhydryl compound mixed with the deoxy-Hb is an amount high enough to increase intramolecular cross-linking of Hb during polymerization and low enough not to significantly decrease intermolecular cross-linking of Hb molecules, due to a high ionic strength. Typically, about one mole of sulfhydryl functional groups (—SH) are needed to oxidation stabilize between about 0.25 moles to about 5 moles of deoxy-Hb.

In a preferred embodiment, the storage buffer contains approximately 25–35 mM sodium phosphate buffer (pH 7.7–7.8) and contains an amount of NAC such that the concentration of NAC in oxidation stabilized deoxy-Hb is between about 0.003% and about 0.3%, by weight. More preferably, the NAC concentration in the oxidation stabilized deoxy-Hb is between about 0.05% and about 0.2% by weight.

Preferably, the storage buffer is filtered prior to mixing with the deoxy-Hb, such as through a 10,000 Dalton ultrafiltration membrane (Millipore Helicon Cat #CDUF050G1 or A/G Technology Maxcell Cat #UFP-10-C-75).

In one embodiment, the oxidation-stabilized deoxy-Hb then flows through an optional filter. Suitable filters include a 0.2 μm polypropylene prefilter (Pall Profile II, Cat#ABIY005Z7) and a 0.2 μm sterile microfilter (Gelman Supor). The deoxy-Hb is maintained under a substantially oxygen-free atmosphere. This can be accomplished, for example, by purging and blanketing the process apparatus with an inert gas, such as nitrogen, prior to and after filling with oxidation-stabilized deoxy-Hb.

Optionally, prior to transferring the oxidation-stabilized deoxy-Hb to polymerization, an appropriate amount of water is added to the polymerization reactor. In one embodiment an appropriate amount of water is that amount which would result in a solution with a concentration of about 10 to about 100 g/l Hb when the oxidation-stabilized deoxy-Hb is added to the polymerization reactor. Preferably, the water is oxygen-depleted.

After the $pO_2$ of the water in the polymerization step is reduced to a level sufficient to limit $HbO_2$ content to about 20%, typically less than about 50 torr, the polymerization reactor is blanketed with an inert gas, such as nitrogen. The oxidation-stabilized deoxy-Hb is then transferred into the polymerization reactor, which is concurrently blanketed with an appropriate flow of an inert gas.

The temperature of the oxidation-stabilized deoxy-Hb solution in polymerization reactor is raised to a temperature to optimize polymerization of the oxidation-stabilized deoxy-Hb when contacted with a cross-linking agent. Typically, the temperature of the oxidation-stabilized deoxy-Hb is about 25° C. to about 45° C., and preferably about 41° C. to about 43° C. throughout polymerization. An example of an acceptable heat transfer means for heating the polymerization reactor is a jacketed heating system which is heated by directing hot ethylene glycol through the jacket.

The oxidation-stabilized deoxy-Hb is then exposed to a suitable cross-linking agent at a temperature sufficient to polymerize the oxidation-stabilized deoxy-Hb to form a solution of polymerized hemoglobin (poly(Hb)) over a period of about 2 hours to about 6 hours.

Examples of suitable cross-linking agents include polyfunctional agents that will cross-link Hb proteins, such as glutaraldehyde, succindialdehyde, activated forms of polyoxyethylene and dextran, $\alpha$-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bis-imidate class, the acyl diazide class or the aryl dihalide class, among others.

A suitable amount of a cross-linking agent is that amount which will permit intramolecular cross-linking to stabilize the Hb and also intermolecular cross-linking to form polymers of Hb, to thereby increase intravascular retention. Typically, a suitable amount of a cross-linking agent is that amount wherein the molar ratio of cross-linking agent to Hb is in excess of about 2:1. Preferably, the molar ratio of cross-linking agent to Hb is between about 20:1 to 40:1.

Preferably, the polymerization is performed in a buffer with a pH between about 7.6 to about 7.9, having a chloride concentration less than or equal to about 35 mmolar.

In a preferred embodiment, a suitable amount of the cross-linking agent is added to the oxidation-stabilized deoxy-Hb which are then mixed by a means for mixing with low shear. A suitable low-shear mixing means includes a static mixer. A suitable static mixer is, for example, a "Kenics" static mixer obtained from Chemineer, Inc.

In one embodiment, recirculating the oxidation-stabilized deoxy-Hb and the cross-linking agent through the static mixer causes turbulent flow conditions with generally uniform mixing of the cross-linking agent with the oxidation-stabilized deoxy-Hb thereby reducing the potential for forming pockets of deoxy-Hb containing high concentrations of the cross-linking agent. Generally uniform mixing of the cross-linking agent and the deoxy-Hb reduces the formation of high molecular weight Hb polymers, i.e. polymers weighing more than 500,000 Daltons, and also permits faster mixing of the cross-linking agent and the deoxy-Hb during polymerization. Furthermore, significant Hb intramolecular cross-linking will result during Hb polymerization due to the presence of a sulfhydryl compound, preferably NAC. While the exact mechanism of the interaction of the sulfhydryl compound with glutaraldehyde and/or Hb is not known, it is presumed that the sulfhydryl compound affects Hb/cross-linking agent chemical bonding in a manner that at least partially inhibits the formation of high molecular weight Hb polymers and preferentially forms stabilized tetrameric Hb.

Poly(Hb) is defined as having significant intramolecular cross-linking if a substantial portion (e.g., at least about 50%) of the Hb molecules are chemically bound in the poly(Hb), and only a small amount, such as less than about 15% are contained within high molecular weight polymerized hemoglobin chains. High molecular weight poly(Hb) molecules are molecules, for example, with a molecular weight above about 500,000 Daltons.

In a preferred embodiment, glutaraldehyde is used as the cross-linking agent. Typically, about 10 to about 70 grams of glutaraldehyde are used per kilogram of oxidation-stabilized deoxy-Hb. More preferably, glutaraldehyde is added over a period of five hours until approximately 29–31 grams of glutaraldehyde are added for each kilogram of oxidation-stabilized deoxy-Hb.

After polymerization, the temperature of the poly(Hb) solution in polymerization reactor is typically reduced to about 15° C. to about 25° C.

Wherein the cross-linking agent used is not an aldehyde, the poly(Hb) formed is generally a stable poly(Hb). Wherein the cross-linking agent used is an aldehyde, the poly(Hb) formed is generally not stable until mixed with a suitable reducing agent to reduce less stable bonds in the poly(Hb) to form more stable bonds. Examples of suitable reducing agents include sodium borohydride, sodium cyanoborohydride, sodium dithionite, trimethylamine, t-butylamine, morpholine borane and pyridine borane. Prior to adding the reducing agent, the poly(Hb) solution is optionally concentrated by ultrafiltration until the concentration of the poly(Hb) solution is increased to between about 75 and about 85 g/l. An example of a suitable ultrafilter is a 30,000 Dalton filter (e.g., Millipore Helicon, Cat #CDUF050LT and Amicon, Cat #540430).

Wherein the reducing agent is borohydride, the pH of the poly(Hb) solution is then adjusted to the alkaline pH range to preserve the reducing agent and to prevent hydrogen gas formation, which can denature Hb during the subsequent reduction. In one embodiment, the pH is adjusted to greater than 10. The pH can be adjusted by adding a buffer solution to the poly(Hb) solution.

Following pH adjustment, at least one reducing agent, preferably a sodium borohydride solution, can be added to the polymerization reactor typically through the deoxygenation loop. Typically, about 5 to about 18 moles of reducing agent are added per mole of Hb tetramer (per 64,000 Daltons of Hb) within the poly(Hb). In a preferred embodiment, for every nine liters of poly(Hb) solution in polymerization subsystem 98, one liter of 0.25M sodium borohydride solution is added at a rate of 0.1 to 0.12 lpm.

The poly(Hb) solution thus formed can be subjected to the hydroxyapatite chromatography, as discussed above. The pH and electrolytes of the stable poly(Hb) can then be restored to physiologic levels to form a stable polymerized hemoglobin blood-substitute, by diafiltering the stable poly(Hb) with a diafiltration solution having a suitable pH and physiologic electrolyte levels. Preferably, the diafiltration solution is a buffer solution.

Wherein the poly(Hb) was reduced by a reducing agent, the diafiltration solution has an acidic pH, preferably between about 4 to about 6.

A non-toxic sulfhydryl compound is also added to the stable poly(Hb) solution as an oxygen scavenger to enhance the stability of the final polymerized hemoglobin blood-substitute. The sulfhydryl compound can be added as part of the diafiltration solution and/or can be added separately. An amount of sulfhydryl compound is added to establish a sulfhydryl concentration which will scavenge oxygen to maintain methemoglobin content less than about 15% over the storage period. Preferably, the sulfhydryl compound is NAC. Typically, the amount of sulfhydryl compound added is an amount sufficient to establish a sulfhydryl concentration between about 0.05% and about 0.2% by weight.

The specifications for a suitable stable polymerized hemoglobin blood-substitute formed by the method of invention are provided in Table I.

TABLE I

| PARAMETER | RESULTS |
| --- | --- |
| pH (18–22° C.) | Physiologically acceptable |
| Endotoxin | Physiologically acceptable |
| Sterility Test | Meets Test |
| Phospholipids[a] | Physiologically acceptable |
| Total Hemoglobin | 10–250 g/l |
| Methemoglobin | <15% |
| Oxyhemoglobin | ≦10% |
| Sodium, Na$^+$ | Physiologically acceptable |
| Potassium, K$^+$ | |
| Chloride, Cl$^-$ | |
| Calcium, Ca$^{++}$ | |
| Boron | |
| Glutaraldehyde | Physiologically acceptable |
| N-acetyl-L-cysteine | Physiologically Acceptable |
| M.W. > 500,000 | ≦15% |
| M.W. ≦ 65,000 | ≦10% |
| M.W. ≦ 32,000 | ≦5% |
| Particulate Content ≧ 10μ | <12/ml |
| Particulate Content ≧ 25μ | <2/ml |

[a]measured in Hb before polymerization

The stable blood-substitute is then stored in a short-term storage container or into sterile storage containers, each having a low oxygen environment. The storage container must also be sufficiently impermeable to water vapor passage to prevent significant concentration of the blood-substitute by evaporation over the storage period. Significant concentration of the blood-substitute is concentration resulting in one or more parameters of the blood-substitute being high out of specification.

Suitable containers include sealed stainless steel and sealed glass containers. Preferably, the storage container is a plastic storage bag which is overwrapped, in a nitrogen atmosphere, using an oxygen barrier composite film incorporating a layer of a metal film, such as aluminum (e.g., KAPAK Type 50303; KAPAK Corporation, Minneapolis, Minn.). Further description of the storage containers is provided in copending U.S. patent application Ser. No. 08/471,583, filed Jun. 7, 1995. These overwrap bags can be sealed with an AUDIONVAC sealing apparatus (Audion Electro B. V., Weesp-Holland).

Optionally, the blood-substitute is directed through a prefilter and microfilter prior to storage. A 0.5 μm or less polypropylene prefilter and a 0.2 μm sterile filter are acceptable as prefilters and microfilters, respectively.

The synthesis of a stable polymerized hemoglobin blood-substitute, formed according to the method of invention, is further described in Example 1.

Vertebrate which can receive the blood-substitute, formed by the methods of the invention include mammals, such as a humans, non-human primates, a dog, a cat, a rat, a horse or a sheep. Further, vertebrates, which can receive said blood-substitute, includes fetuses (prenatal vertebrate), postnatal vertebrates, or vertebrates at time of birth.

A blood-substitute of the present invention can be administered into the circulatory system by injecting the blood-substitute directly and/or indirectly into the circulatory system of the vertebrate, by one or more injection methods.

Examples of direct injection methods include intravascular injections, such as intravenous and intra-arterial injections, and intracardiac injections. Examples of indirect injection methods include intraperitoneal injections, subcutaneous injections, such that the blood-substitute will be transported by the lymph system into the circulatory system, injections into the bone marrow by means of a trocar or catheter. Preferably, the blood-substitute is administered intravenously.

The vertebrate being treated can be normovolemic, hypervolemic or hypovolemic prior to, during, and/or after infusion of the blood-substitute. The blood-substitute can be directed into the circulatory system by methods such as top loading and by exchange methods.

A blood-substitute can be administered, therapeutically, to treat hypoxic tissue within a vertebrate resulting from many different causes including reduced RBC flow in a portion of, or throughout, the circulatory system, anemia and shock. Further, the blood-substitute can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to therapeutically or prophylactically treat hypoxia, particularly from a partial arterial obstruction or from a partial blockage in microcirculation, and the dosages used therein, is provided copending U.S. patent application Ser. No. 08/409,337, filed Mar. 23, 1995, which is incorporated herein by reference in its entirety.

Typically, a suitable dose, or combination of doses of blood-substitute, is an amount which when contained within the blood plasma will result in a total hemoglobin concentration in the vertebrate's blood between about 0.1 to about 10 grams Hb/dl, or more, if required to make up for large volume blood losses.

Equivalents

Those skilled in the art will recognize, or be able to ascertain using no more than routine experimentation, many equivalents to the specific embodiments of the invention described herein. These and all other such equivalents are intended to be encompassed by the following claims.

The invention claimed is:

1. A method for separating a polymerized hemoglobin from a polymerized hemoglobin solution containing polymerized hemoglobin and non-polymerized hemoglobin, comprising subjecting the solution to a hydroxyapatite packed chromatography column, and recovering the polymerized hemoglobin.

2. The method of claim 1 wherein the chromatography is a high performance liquid chromatography.

3. The method of claim 2 further comprising the step of polymerizing a substantially pure hemoglobin solution, thereby preparing the polymerized hemoglobin solution containing polymerized and non-polymerized hemoglobin.

4. The method of claim 3 wherein the polymerization is performed in the presence of a cross-linking agent.

5. The method of claim 4 wherein the cross-linking agent is a dialdehyde.

6. The method of claim 5 wherein the dialdehyde is glutaraldehyde.

7. The method of claim 5 wherein the cross-linking agent is a dialdehyde and wherein the polymerized hemoglobin solution contains unstable groups, further comprising the steps of:

a) contacting the polymerized hemoglobin solution with an alkaline solution, whereby the polymerized hemoglobin solution is basified; and b) contacting the basified polymerized hemoglobin solution with a reducing agent, whereby unstable bonds are reduced, thereby forming a stable polymerized hemoglobin solution.

8. The method of claim 7 wherein said reducing agent comprises sodium borohydride.

9. The method of claim 3 further comprising the step of maintaining polymerization under a low oxygen environment.

10. The method of claim 3 wherein said substantially pure hemoglobin solution is ultrapure.

11. The method of claim 3 wherein the substantially pure hemoglobin solution is derived from blood that is selected from a group consisting of human blood, bovine blood, primate blood, ovine blood, porcine blood and transgenically produced blood.

12. A method for producing an ultrapure stable polymerized hemoglobin blood-substitute, wherein said blood-substitute can be administered to humans or other vertebrates, comprising the steps of:

a) mixing a mammalian blood with an anticoagulant to form a blood solution;
   b) diluting the blood solution with an isotonic solution;
   c) filtering said diluted blood solution to separate smaller plasma components from the red blood cells;
   d) centrifuging said filtered blood solution to separate white blood cells from the red blood cells;
   e) directing the red blood cells against a surface to tear the cell membranes of at least a portion of the red blood cells to form a hemoglobin solution;
   f) ultrafiltering the hemoglobin solution to remove large cell debris from the hemoglobin solution;
   g) ultrafiltering the hemoglobin solution to remove small cell debris from the hemoglobin solution;
   h) chromatographically treating said filtered hemoglobin solution by high performance liquid chromatography employing a pH gradient elution and a packing for the ion-exchange affinity separation f endotoxin from hemoglobin to form an ultrapure hemoglobin eluate;
   i) deoxygenating said ultrapure hemoglobin eluate to form a deoxygenated hemoglobin solution;
   j) mixing said deoxygenated hemoglobin solution with a sulfhydryl compound, to form an oxidation-stabilized, deoxygenated hemoglobin solution;
   k) mixing said oxidation-stabilized, deoxygenated hemoglobin solution with a cross-linking agent to form a polymerization reaction mixture; and
   l) polymerizing the polymerization reaction mixture, thereby forming a polymerized hemoglobin solution;
   m) contacting the polymerized hemoglobin solution with an alkaline solution, whereby the polymerized hemoglobin solution is basified;
   n) contacting the basified polymerized hemoglobin solution with sodium borohydride, whereby unstable bonds are reduced, thereby forming a stable polymerized hemoglobin solution; and
   o) contacting the stable polymerized hemoglobin solution with a hydroxyapatite HPLC column, whereby polymerized hemoglobin is separated from non-polymerized hemoglobin, thereby forming said ultrapure stable polymerized hemoglobin blood-substitute.

13. A stable polymerized hemoglobin blood-substitute prepared according to the method of claim 1.

14. A stable ultrapure polymerized hemoglobin blood-substitute prepared according to the method of claim 12.

15. A blood-substitute of claim 14 wherein the hemoglobin is selected from a group consisting of human hemoglobin, bovine hemoglobin, primate hemoglobin, ovine hemoglobin, porcine hemoglobin, and transgenically produced hemoglobin and recombinantly produced hemoglobin.

16. A method for increasing tissue oxygenation in tissue of a vertebrate subject, comprising the step of introducing into the circulatory system of the vertebrate an effective amount of stable polymerized hemoglobin blood-substitute prepared according to claim 1.

17. A method for increasing tissue oxygenation in the tissue of a human, without significant side effects, comprising the step of introducing into the circulatory system of the human a stable polymerized hemoglobin blood-substitute prepared according to claim 1.

18. A method of claim 17 wherein said hemoglobin blood-substitute is derived from bovine blood.

\* \* \* \* \*